United States Patent [19]

Kamp et al.

[11] 4,066,898

[45] Jan. 3, 1978

[54] METHOD AND APPARATUS FOR MONITORING AMOUNT OF A SUBSTANCE APPLIED TO A FABRIC

[75] Inventors: Arthur J. Kamp; Philip G. Mischler, both of Midland, Mich.

[73] Assignee: The Dow Chemical Company, Midland, Mich.

[21] Appl. No.: 676,036

[22] Filed: Apr. 12, 1976

[51] Int. Cl.² ............................................. G01N 23/00
[52] U.S. Cl. .................................................. 250/359
[58] Field of Search ................... 250/358 R, 359, 360, 250/272, 273, 303

[56] References Cited

U.S. PATENT DOCUMENTS

| | | | |
|---|---|---|---|
| 3,270,200 | 8/1966 | Rhodes | 250/358 X |
| 3,938,955 | 2/1976 | Maggiolo | 250/303 X |

OTHER PUBLICATIONS

"An X-ray Absorption Technique for Measurement of Coat Weight on Paper," Murray et al., Advan. X-ray Anal., 1961, pp. 309–318.

*Primary Examiner*—Davis L. Willis
*Attorney, Agent, or Firm*—Burke M. Halldorson

[57] ABSTRACT

An apparatus and method based on X-ray transmission is disclosed for determining the thickness, or equivalently, the weight per unit area, of a substance containing atoms of a non-radioactive element of atomic number of 11 or greater applied to a fabric, such as a calcium- and/or aluminum-containing latex coating on a carpet. The apparatus employs a source of radiation which emits a single predominant X-ray within the range of 12–19 Kev, such as zirconium which fluoresces at 16 Kev when bombarded with 60 Kev radiation from americium-241; a detector sensitive to the radiation emitted and having resolution at least as sharp as about 20 percent, such as a $Kr/CO_2$ proportional counter; and a suitable electronic circuit to convert the charge pulse output of the detector to a readout signal related to the amount of the substance on the fabric.

45 Claims, 6 Drawing Figures

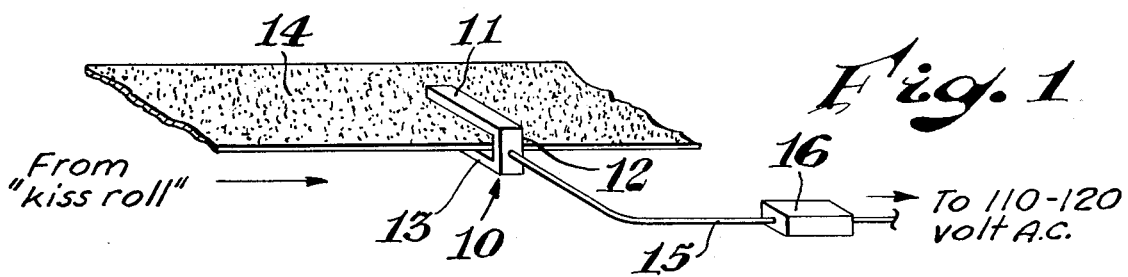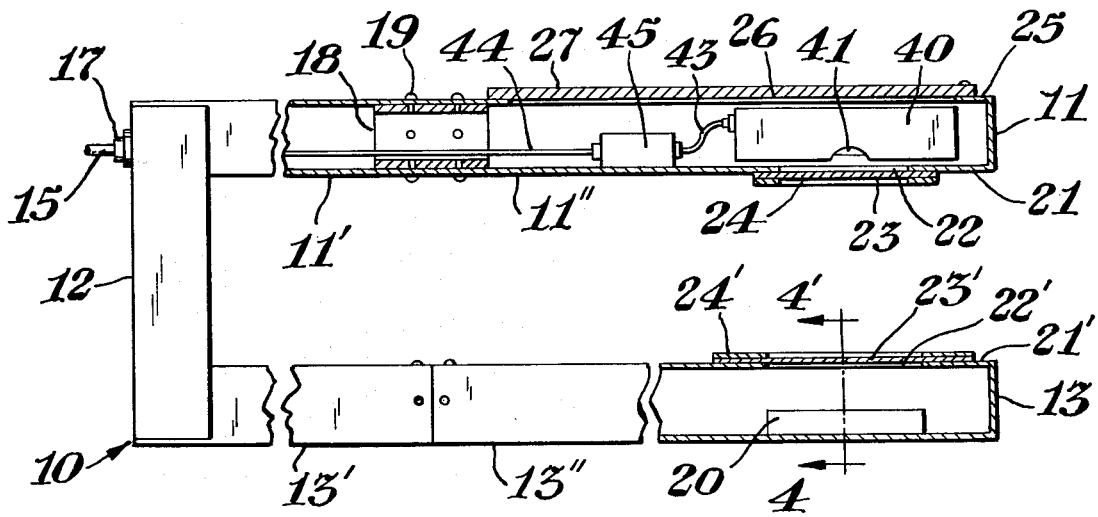

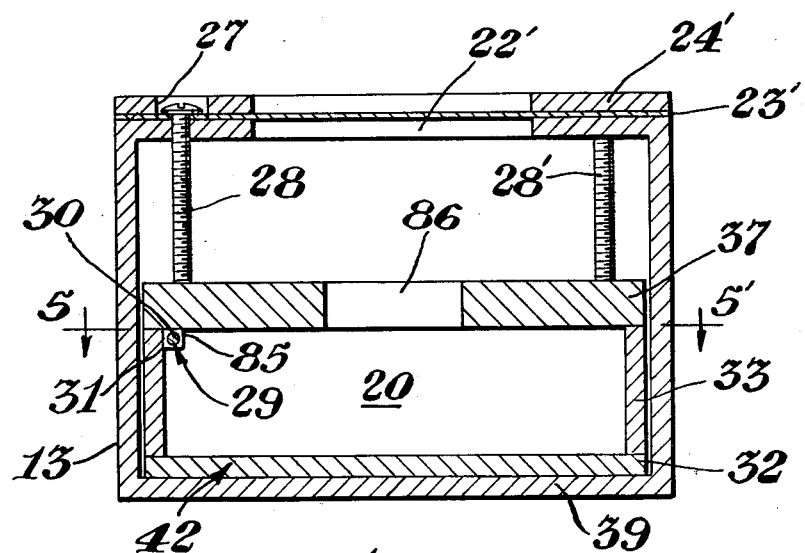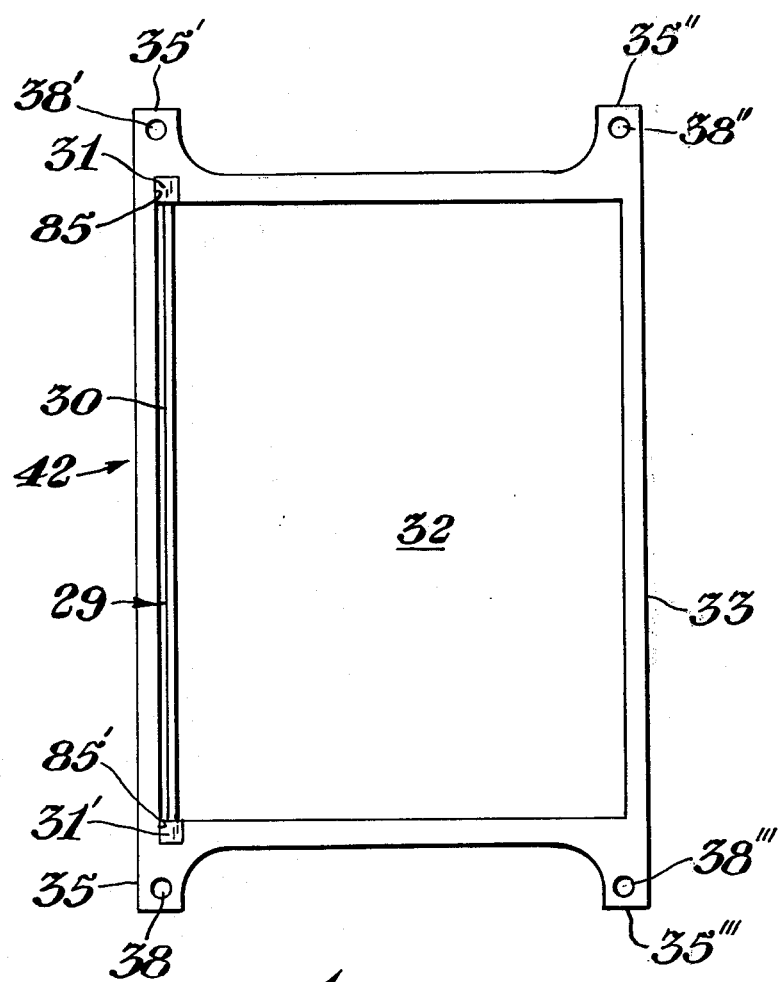

METHOD AND APPARATUS FOR MONITORING AMOUNT OF A SUBSTANCE APPLIED TO A FABRIC

BACKGROUND OF THE INVENTION

A. Field of the Invention

This apparatus relates to a method and apparatus for measuring the amount of a substance containing atoms of a non-radioactive element of atomic number of 11 or greater on a fabric using X-ray transmission, particularly where the fabric is a carpet and the coating is a calcium-and/or aluminum-containing latex coating.

B. Description of the Prior Art

In the manufacture of conventional carpets, a styrene-butadiene based latex is used to adhere the various components of the carpet together. A typical latex formulation comprises, by weight, about 55 percent calcium carbonate, about 15 percent a styrene-butadiene-itaconic acid terpolymer, and about 30 percent water. In other latex formulations, all or a part of the calcium carbonate may be replaced by alumina trihydrate. In a representative manufacturing process, the yarn, which eventually forms the carpet nap, is tufted into a jute or polypropylene primary backing, the latex is coated on the back of the primary backing, and a second jute or polypropylene backing is then applied. Finally, the carpet is dried. The latex layer serves as a binder which holds the yarn tufts and the second backing in place. Immediately after application of the latex, the partially completed carpet may contain from about 5–80 ounces per square yard (15–270 mg/cm$^2$) of fabric and about 20–60 ounces per square yard (70–200 mg/cm$^2$) of wet latex.

Since carpet quality is critically dependent on the latex binder, a precise, reliable instrument for non-destructibly monitoring the amount of latex applied would be quite useful to the carpet manufacturer. Moreover, a portable instrument, readily adapted for interstate transportation in, for example, an automobile, would be a valuable asset for technical assistance representatives of latex vendors.

The term "amount" of latex is used herein because the technical term of art employed in the carpet industry is somewhat of a misnomer: it is common to express the average "thickness" of the latex coating, not in linear units, but rather in terms of weight of latex per unit area of the carpet, e.g. ounces per yard or mg/cm$^2$. Since the specific gravity of the latex can readily be determined, however, it is a simple matter to convert from units of mass per unit area to linear units, and vice versa.

It is reported by J. F. Cameron et al. in Radioisotope Instruments, Part I, page 153, Pergamon Press, New York, 1971, that beta-gauges before and after the "kiss roll" used to apply the latex make it possible to control the amount of latex applied. Beta-gauges, however, whether based on scattering or transmission phenomena, present rather serious radiation hazards. Moreover, the results are significantly affected by the carpet matrix, i.e., by the components of the carpet other than the latex formulation. Consequently, the accuracy and precision of beta gauges is marginal. For these reasons, beta gauges are not normally used in the carpet industry. For a lack of a better instrument, the instrument believed most widely used at present for measuring the amount of latex applied to a carpet, is based on microwave absorption. Microwave absorption is a function of water content, water being one of the components in a latex formulation. Even this instrument and method, however, suffer from several sources of error and are not well accepted by the industry.

Other approaches to the problem have been considered but found wanting in at least one respect. X-ray fluorescence, for example, was disclosed by Nelson et al. in Textile Research Journal, pp. 357–361 (June, 1973) as a method for determining the amount of a bromine compound on a fabric, but fluorescence is not universally suitable for coatings of the thicknesses encountered in carpet applications. X-ray scattering is much affected by the matrix, and the results obtained would suffer unacceptably from a lack of precision and accuracy.

Radiation transmission, and in particular X-ray transmission, has been used in other applications for determining the thickness of objects, and even for determining the thickness of various coatings on objects.

Friedman, U.S. Pat. No. 2,462,088 discusses early methods, based on X-ray transmission or back radiation, for measuring the thickness of heavy steel sections and pipe walls, and then discloses a method for accomplishing the same objective wherein the beam of radiation is directed perpendicular to the radius of curvature of the pipe and in a plane perpendicular to the longitudinal axis of the pipe, and wherein the thickness of the pipe wall, which may be of several layers, is measured by determining sharp variations in the amount of X-rays transmitted to a detector as a function of the position of the radiation beam along the radius of curvature of the pipe. Wolf, U.S. Pat. No. 2,486,902; Herzog, U.S. Pat. No. 2,540,261; McKee, U.S. Pat. No. 2,702,864; and O'Shea et al., U.S. Pat. No. 3,426,196 also disclose use of radiation to measure the thickness of pipes or other curved walls.

Herzog, in U.S. Pat. Nos. 2,501,173 and 2,528,724, discloses a device and method for measuring the thickness of curved objects such as hollow propeller blades using a homogeneous source of gamma radiation and a detector therefor mounted on a pantograph frame in a manner such that the respective housings for the source and detector can be maintained against the respective internal and external surfaces of the object being measured. Herzog also teaches measurement of the density of a fluid in a container using radiation transmission in U.S. Pat. No. 2,501,174.

Apparatus and/or methods for measuring the thickness of moving metal strips by radiation transmission are taught by McNamara, U.S. Pat. No. 3,179,800; and Busch et al., U.S. Pat. No. 3,715,592.

Apparatus and/or methods for determining coating thicknesses on material other than carpeting using radiation transmission are disclosed by Zemany, 30 Rev. Sci, Instr. 292-3 (1959) — titanium films on Kovar alloy; and Murray, 4 Advan. X-ray Anal. 309-18 (1961) — Kaolin coating clay on paper.

Apparatus and/or methods using radiation for determining the density, thickness, or concentration of other miscellaneous materials are disclosed by: Rhodes, U.S. Pat. No. 3,270,200 — concentration of an element in a mixture; Duftschmidt et al., U.S. Pat. No. 3,497,693 — discontinuous materials such as asbestos-cement sheets, plastic sheets, or glass sheets; Roller et al., U.S. 3,796,874 — cable insulation; Dragonette, U.S. Pat. No. 3,531,827 — plastic sheets; Gladstone, Paper-Maker, Wiggins, Teape & Co. Ltd., London 1956, No. 4–7, abstracted at 50 Chem. Abstracts 13442b; Barta et al., 14

Energia Atomtech. 570-575 (1961), abstracted at 58 Chem. Abstracts 209f — wall thickness of oxygen cylinders, Joffe et al., U.S. Pat. No. 3,319,067; and Australian Pat. No. 263,677.

Initial attempts at employing X-ray transmission for measurement of the amount of latex applied in the manufacture of carpeting proved commercially unacceptable. In particular, the accuracy and precision obtained was not satisfactory when filtered radiation from a linear array of plutonium-238 was used as a radiation source, in combination with a calcium fluoride scintillation detector coupled to a light pipe and a photo multiplier tube as the means for detecting the transmitted radiation. Even when filtered, several different X-rays of similar energies were nevertheless emitted from such a source, and, since the lower energy X-rays were more readily absorbed than those of higher energies, the percent of radiation transmitted was not a truly exponential function of thickness.

Summary of the Invention

In its broadest aspects, the present invention comprises a method for measuring the amount of a substance in, or equivalently, on, a fabric matrix, wherein the substance contains atoms of a non-radioactive element of atomic number of 11 or greater, such as the amount of a calcium- or aluminum-containing latex applied to a carpet, and an apparatus particularly adapted to carrying out the method.

The apparatus employs a particular source of electromagnetic radiation, a particular detector sensitive to the incident radiation, and a suitable electronic circuit means for relating the detector output to the amount of substance in the matrix, preferably linearly. More particularly, the source of radiation is one which, within the range of about 12 to about 19 kiloelectron volts (Kev), emits a single predominant, monoenergetic radiation. The detector is a charge pulse detector which has a resolution of at least as sharp as about 20 percent, as hereinafter defined, within the range of from about 12-19 (Kev), which detector is sensitive to the predominant radiation from the source. The detector is spaced apart from the source and aligned so as to receive radiation from the source. In response to radiation incident thereupon, the detector generates a pulse output which varies in amplitude with the energy of the incident radiation. Although permanently installed devices using similar components in a similar manner are within the scope of the present invention, a preferred embodiment is a relatively light weight device which can readily be transported and carried about by one individual.

The method of the present invention comprises providing a source of radiation which emits, within the range of from about 12 to about 19 Kev, a single predominant non-energetic electromagnetic radiation; exposing the substance-containing fabric matrix to said source; selectively detecting the amount of the predominant radiation transmitted through the fabric and generating an electrical signal in response thereto; and relating the electrical signal to the amount of substance in the matrix, preferably in a linear output.

BRIEF DESCRIPTION OF THE DRAWINGS

FIG. 1 shows a schematic view in perspective of one embodiment of the apparatus of this invention, in a position suitable for determining the amount of latex applied to a moving carpet by a "kiss roll."

FIG. 2 is a side plan view, partially broken away and in section, showing a probe 10 housing a source 20, a detector 40, and preamp transducer 45 for converting the pulsed current output of the detector 40 to a pulsed voltage signal.

FIG. 3 is a transparent view in perspective of a portion of source arm 13 which shows, in dotted lines, the exterior of one embodiment of source 20 housed within source arm 13.

FIG. 4 is a cross section view of source arm 13 taken along the plane indicated by line 4-4' in FIG. 2.

FIG. 5 is a top plan view of one embodiment of the interior of source 20 taken along the plane of line 5-5' in FIG. 4.

FURTHER DESCRIPTION OF THE INVENTION

Figure 6:
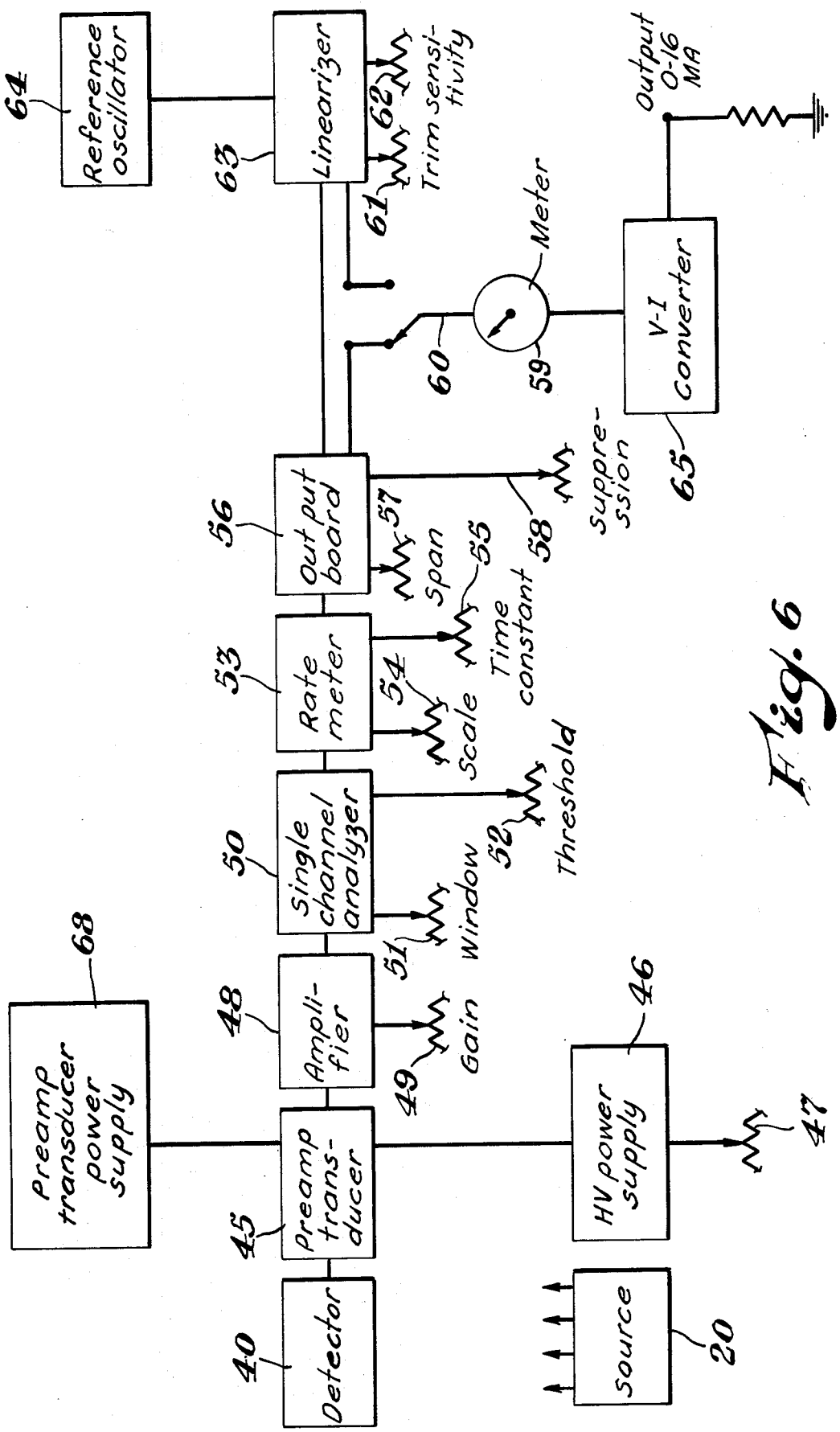
FIG. 6 is a block schematic representation of a suitable circuit for relating the output of detector 40 to the amount of substance between the source 20 and detector 40.

The substance which is detected according to the method of the present invention may be a liquid, a gel, a solid, or a mixture of substantially uniformly dispersed finely divided solids in a liquid or in a gel or in another solid. The substance must include a non-radioactive element of atomic number 11 or greater. The form in which the element is present is not critical; it may be present in elemental form, in a compound, or both. The substance may contain one, or more than one, such element. For example, the substance may be a wet, dry, or partially dried latex coating as hereinabove described containing calcium, e.g. as calcium carbonate, or aluminum, e.g. as alumina trihydrate, or both.

Referring to FIG. 1, there is shown a moving segment of carpet 14 travelling from left to right as illustrated, which has had a layer of, for example, calcium-containing latex applied to its undersurface by one or a series of kiss rolls. A probe 10, which is generally of a "lazy block U" shape, is shown having: a detector (or, as illustrated, upper) arm 11 which houses a radiation detector 40 (shown in FIG. 2) as hereinafter described; spaced apart from said detector arm 11 and parallel thereto, a source (or, as illustrated, lower) arm 13 which houses a source 20 (FIG. 2); and joining said arms at one end thereof, a vertical support 12. Although not critical to the invention, in the embodiment shown, the arms 11 and 13 and support 12 are hollow tubular members having a rectangular cross section, and are preferably constructed of a light weight material such as aluminum. As shown in FIG. 2, each arm is closed at its distal end i.e., the end not jointed to the vertical support 12. The probe 10 is positioned so that the arms 11 and 13 are substantially parallel to the plane of the moving carpet, with the carpet passing between the two arms without the carpet coming into contact with either arm. The probe 10 is connected through electrical connecter 17 and electrical cable 15 to an electric circuit board and readout means, shown schematically as 16 in FIG. 1, which in turn is connected to a source of 110-120 volt 60 Hertz current. Other common AC power sources such as 220 volt 50 Hertz current may also be used.

As shown in FIG. 2, the detector 40, which has a window 41, and the source 20 are positioned near the distal end of the respective arms 11 and 13. The detector 40 is connected to a preamp transducer 45, also housed in arm 11, by cable 43, and the transducer 45 is in turn connected to cable 15 through cable 44 and connecter 17. The arms 11 and 13 may be constructed of one or more segments such as 11' and 11", and 13' and 13", any number of which may be joined together in a conventional manner such as by a connecter and bolts as shown at 18 and 19, respectively, to make each arm whatever length may be desired. The surface 21 of arm 11 which is nearest arm 13 is provided with an aperture 22 aligned with detector window 41 so that radiation from the source 20 can pass into arm 11 and then into detector window 41. A protective sheet 23 of material which is transparent to the radiation of the source may be provided over aperture 22 and held in place by retainer 24, if desired. A similar aperture 22', protective sheet 23' and retainer 24', held in position by screws such as screw 87 (FIG. 3), are provided in the surface 21' of arm 13 over the source 20. Optionally, the surface 25 of arm 11 furthest from arm 13 may be provided with an aperture 26 and removable lid 27 to facilitate access to detector 40, transducer 45, and cables 43 and 44.

The radiation source must be one which provides, somewhere within the range of from about 12 Kev to about 19 Kev, a predominant, substantially monoenergetic emission, preferably at about 16 Kev. If the energy of the radiation, usually an X-ray, is too high, the absorption coefficient for the latex will be too low to permit detection of slight changes in the amount of latex on the fabric, or in less severe cases, the difference between the absorption coefficient for the fabric and the latex will not be sufficiently great, so that a slight change in the fabric matrix will result in relatively significant change in the percent radiation transmitted. On the other hand, at too low an energy, very slight changes in the thickness of latex at low thicknesses will effect a large change in percent radiation transmitted relative to a similar percentage change in the carpet fabric, which in itself would be desirable, but for the fact that the absolute value for the exponential term in the absorption relationship $$I_t = I_o e^{(-\mu_c \rho_c \tau_c - \mu_L \rho_L \tau_L)}$$

where
- $I_t$ = intensity of transmitted radiation,
- $I_o$ = intensity of incident radiation
- $\mu$ = mass absorption coefficient, cm$^2$/g
- $\rho$ = material density, g/cm$^3$
- $\tau$ = thickness, cm
- subscript $c$ = carpet
- subscript $L$ = latex becomes so large at the higher latex thicknesses that the percent radiation transmitted is so low that slight changes in the amount of latex applied cannot be discerned. Generally, it is preferable that the energy be selected so that the exponential term will lie within the range of from about −0.5 to about −2.3 over the entire range of the latex and carpet thicknesses likely to be encountered, i.e. so that $I_t$ is from about 10 to about 60 percent of $I_o$.

As hereinabove mentioned, the photons emitted by the source in the indicated energy range must be substantially monoenergetic: broad band or bremsstrahlung emissions are not suitable, because of interference which can affect the accuracy of the results. Moreover, the results using such a broad band source cannot be linearized by conventional means, because the percent radiation transmitted is not a truly exponential function of thickness as hereinabove discussed under the "Background of the Invention" caption.

Such substantially monoenergetic radiation can be provided by using a primary source incident upon a target which in turn fluoresces at an energy having the characteristics hereinabove described. The primary source emits a predominant radiation at greater than about 19 Kev, preferably at an energy about 2 to 10 times the energy of the radiation which fluoresces from the target; too high an energy emission from the primary source results in an increased safety risk and/or the need to implement an additional safety precaution, whereas too low a ratio of primary source energy:target fluorescence energy can result in interference, since at least a small amount of the primary source radiation will almost inevitably escape or reflect from the target, pass through the sample being measured, and enter the detector. The primary source preferably has a long half life, i.e., 10 years or more, so that the rate of emission remains virtually unchanged. A preferred primary source having all of these characteristics is americium-241 which has a half life of about 460 years and emits a relatively intense gamma ray at 59.57 Kev.

The target must fluoresce at a single predominant energy within the range of about 12-19 Kev when excited by the radiation of the primary source. A preferred target material is zirconium which fluoresces at about 16 Kev. Those skilled in the art will be able to select other elements and compounds for use as a target as may be desired, since it is known that the energy of the fluorescent X-ray is a function of the atomic number of the element. Bromine, for example, fluoresces at about 12 Kev and may be used as a target, e.g., as a pellet or coating on a substrate in the form a bromide salt or an organic bromide compound. Zirconium is preferred, however, inasmuch as it fluoresces at a very suitable energy, is readily available, is adequately stable in the presence of atmospheric moisture, and is easily formable into convenient shapes. When used at an adequate thickness, it also sufficiently shields escape of the radiation from the primary source.

FIGS. 3-5 illustrate a preferred embodiment for the construction, assembly, and positioning of an americium-241 and zirconium source. The primary source 29 is a sealed stainless steel tube 30 containing a suitable amount, e.g. 500 millicurie, of americium-241 oxide. At either end of tube 30 are mounting tabs 31 and 31' which have the shape of rectangular prisms. The target is a box-like member 42, constructed of zirconium, having a base plate 32, a seamless upright member 33 defining the walls of the box, and a cover member 37. The outer perimeter of base plate 32, upright member 33, and cover member 37 are congruent with one another, each having ears 34-34''', 35-35''' and 36-36''' at each corner for receiving means such as bolts 38-38''' for fastening the cover member 37, upright member 33, and base plate 32 together. If desired, bolts 38-38''' may extend through base plate 32 into the floor 39 of arm 13, thereby removably securing the source 20 in the source arm 13. Alternatively, source 20 may be secured in position by one or more set screws, such as 28 and 28' mounted in surface 21'. In the embodiment shown in FIGS. 3 and 4, holes 27 and 27' are provided in retainer 24' of slightly greater diameter than the head of each set screw 28 and 28' so that the retainer 24' may be removed, if desired, without disturbing the source 20. Referring to FIGS. 4 and 5, the primary source 29 is mounted by means of tabs 31 and 31' in the interior of box 42 near and parallel to one of the two interior edges defined by the cover member 37 and one of the two walls of upright member 33 which is parallel to the plane defined by arms 11 and 13. Tabs 31 and 31' are inserted into notches 85 and 85' provided at the interior of, and near the top of, ears 35 and 35'. Cover member 37, which holds tabs 31 and 31' into notches 85 and 85' when in position, is provided with slit 86 which is parallel to primary source 29. As illustrated in FIG. 4, it is preferred to employ a cover member 37 of somewhat greater thickness than the minimum required to absorb the gamma rays of the primary source 30, in order to help collimate the X-rays leaving slit 86. Other configurations for source 20 may also be used. The configuration described, however, provides a uniform pattern of X-rays with a minimum amount of gamma ray reflection.

The detector employed herein must have good ability to resolve different energies within the range of from about 12 to about 19 Kev, i.e., at least as sharp as about 20 percent resolution, such as is obtained with noble gas-type radiation detectors. By resolution is meant on a plot of counts per second vs. the detector output after conversion from current to voltage and suitable amplification, the percentage ratio of the full width of a peak at midheight, to the position of the peak on the abscissa; in other words, the lower the percent figure, the sharper the resolution. The resolution of crystal detectors such as calcium fluoride scintillation detectors in combination with photo multiplier tubes is typically on the order of about 50 percent or higher, and such detectors are not suitable for use herein. Representative of detectors which are suitable for use herein are the type having a high voltage wire suspended in a chamber containing predominantly, e.g., 95–99 percent, a noble gas, and the balance substantially carbon dioxide. Most preferred is a $Kr/CO_2$ detector. Such a detector has a high counting efficiency for X-rays in the 12–19 Kev range and relatively low efficiency for radiation on the order of 60 Kev. Use of this type of detector minimizes the significance of the fact that approximately 10 percent of the radiation emitted from the slit in the preferred source hereinabove described is 60 Kev radiation directly from the americium-241 primary source. Xenon/carbon dioxide detectors are somewhat less desirable in that the efficiency of such detectors for 16 Kev X-rays is about the same as that of the krypton detector, but the xenon detector picks up 60 Kev emissions more efficiently. The ratio of sensitivity to the lower energy radiation is about the same in argon detectors as in krypton detectors, but the argon detector is a much less efficient detector of both the 16 and 60 Kev radiation.

In operation, the detector 40 produces a current pulse each time it detects an event, the magnitude of the pulse increasing with the energy of the incident photon. Referring now to FIG. 6, the current pulse is fed through a conventional preamp transducer 45, the principle function of which is to convert the current pulse to a voltage pulse. Transducer 45 may conveniently be housed in detector arm 11 as shown in FIG. 2.

High voltage ranging up to about 1800 volts, as adjusted by potentiometer 47, is provided to the detector 40 and preamp transducer 45 by a high voltage power supply 46. Low voltage is supplied to the preamp transducer 45 by power supply 68, such as an Ortec brand model 114 power supply.

The output pulse signal from preamp transducer 45, which pulses are on the order of up to several tenths of a volt, are fed into amplifier 48, which puts out voltage pulses on the order of several volts. The amplifier output may be adjusted by gain control 49.

To screen out signals generated as result of detection of X-rays of an energy other than that of principle interest emitted from source 20, e.g., the approximately 60 Kev radiation of americium-241, the amplifier output is next fed into a conventional single channel analyzer circuit 50 having threshold 52 and window 51 adjustments. Threshold adjustment 52 is set so that X-rays having lower energies than the X-ray of interest will generate no output from analyzer 50, and window adjustment 51 screens out voltage peaks greater than that generated by the X-ray of interest.

Voltage pulses not rejected by the analyzer 50 are provided as input to a conventional ratemeter circuit 53, which converts a pulse frequency to an analog voltage. The ratemeter may optionally contain scale 54 and time consant 55 adjustments which may be used to count only a fraction of input pulses, and to determine the period of time over which the pulses are counted.

Next, the analog signal is fed to an output board 56 where the signal is suppressed by potentiometer 58, adjusted in span by potentiometer 57, and inverted. Suppression permits zeroing of the instrument when a fabric having no latex is positioned between the source 20 and the detector 40. After setting the suppression to zero for an uncoated fabric, a sample of the same fabric except having a known quantity of latex coating in an amount somewhat greater than the maximum amount anticipated to be encountered on an unknown sample of the fabric, is placed between the source 20 and the detector 40, and the span is adjusted to full scale. Because the addition of latex decreases the radiation signal picked up by the detector 40, the signal is inverted to give an increase in output corresponding to increasing amounts of latex coating. The output from output board 56 is exponentially related to the amount of coating on the fabric, and the output may be fed for readout through switch 60 to readout means, which may be for example, visible readout means such as conventional dial voltmeter as shown at 59, a digital voltmeter, or a strip chart recorder, or means such as an audible alarm system, a computer data storage bank, or the like. If desired, the voltage signal can further be converted to current in a V-I converter circuit 65.

Rather than feed the output from the output board 56 directly to the readout means, however, it is much preferred to first linearize the signal in a standard linearizer circuit 63. A reference oscillator 64 may be provided for linearizer 63 for use where line frequencies vary; normally, however, the linearizer is referenced to the line frequency. The linearizer converts the exponential analog voltage output of the output board 56 to a linear function which varies directly with the amount of latex on the fabric. By proper adjustment of the trim 61 and sensitivity 62 controls, and connection of the readout means through switch 60 to the linearizer 63, the readout can be adjusted so that the amount of latex can be read directly in whatever units may be desired, e.g., ounces per yard.

What is claimed is:
1. An apparatus capable of determining the amount of a substance applied to a fabric matrix, said substance being characterized as containing atoms of a non-radioactive element of atomic number 11 or greater, comprising:
   a. a source of radiation which, within the range of from about 12 to about 19 Kev, emits a single predominant, monoenergetic radiation;

b. spaced apart from the source and aligned so as to receive radiation from the source, a charge pulse detector having a resolution at least as sharp as about 20 percent, within the range of from about 12-19 Kev, which detector is sensitive to the predominant radiation from the source and which generates a pulse output which varies in amplitude with the energy of the instant radiation, said matrix being positioned between the source and the detector;

c. readout means; and d. electronic circuit means connected to said detector for relating the detector output to the amount of substance in the matrix, and for generating a signal in said readout means in response to said relationship.

2. The apparatus of claim 1 wherein said matrix is a carpet, said substance is a latex coating and said non-radioactive element is selected from a group consisting essentially of calcium, aluminum or mixtures thereof.

3. The apparatus of claim 1 wherein component (c) is a means for providing a visible readout.

4. The apparatus of claim 1 wherein component (d) includes means for converting the pulsed output to an analog signal.

5. The apparatus of claim 1 wherein component (d) includes adjustable means for generating a zero signal in said readout means when a matrix known to be substantially free of said substance is placed between the source and the detector.

6. The apparatus of claim 1 wherein component (d) includes means for electronically rejecting detector output resulting from detection of radiation having an energy less than a first preselected level and greater than a scond preselected level.

7. The apparatus of claim 1 wherein component (d) include means for linearly relating the detector output to the amount of said substance in the matrix.

8. The apparatus of claim 7 wherein component (d) includes between the detector and the means for linearly relating, means for converting the pulsed output of the detector to an analog signal, means for inverting the analog signal, and means for adjusting the analog signal to generate a zero signal when a matrix known to be substantially free of said substance is placed between the source and the detector.

9. The apparatus of claim 8 wherein component (d) includes between the detector and the means for converting, means for electronically rejecting detector output result from detection of radiation having an energy less than a first preselected level and greater than a second preselected level.

10. The apparatus of claim 1 wherein the detector is of the type having a high voltage wire suspended in a chamber containing an atmosphere predominantly of a noble gas and the balance, carbon dioxide.

11. The apparatus of claim 10 wherein the noble gas is krypton.

12. The apparatus of claim 1 wherein component (a) includes a primary source of radiation having an energy greater than about 19 Kev and a target which fluoresces when exposed to the primary source to produce the monoenergetic radiation within the range of from about 12 to about 19 Kev.

13. The apparatus of claim 12 wherein the energy of the predominant radiation of the primary source is from about 2 to about 10 times the energy of the monoenergetic radiation of the target, and wherein the half life of the primary source is at least about 10 years.

14. The apparatus of claim 13 wherein the primary source contains americium-241, or a compound thereof.

15. The apparatus of claim 14 wherein the target is zirconium.

16. The apparatus of claim 15 wherein component (d) includes means for linearly relating the detector output to the amount of substance in the matrix.

17. The apparatus of claim 16 wherein component (d) includes, between the detector and the means for linearly relating, means for converting the pulsed output of the detector to an analog signal, means for inverting the analog signal, and means for adjusting the analog signal to generate a zero signal when a matrix known to be substantially free of said substance is placed between the source and the detector.

18. The apparatus of claim 17 wherein component (d) includes between the detector and the means for converting means for electronically rejecting detector output resulting from detection of radiation having an energy less than a first preselected level and greater than a second preselected level.

19. The apparatus of claim 15 wherein the detector is of the type having a high voltage wire suspended in a chamber containing an atmosphere predominantly of a noble gas and the balance, carbon dioxide.

20. The apparatus of claim 19 wherein the noble gas is krypton.

21. The apparatus of claim 20 wherein said substance is a latex coating, said matrix is a moving segment of carpet, said non-radioactive element is selected from a group consisting essentially of a calcium compound, an aluminum compound or mixtures thereof, said readout means provides a visible readout and said electronic circuit means includes means for electronically rejecting detector output resulting from detection of radiation having an energy less than a first preselected level and greater than a second preselected level, means for converting the output from the detector not rejected to an analog signal, means for inverting the analog signal and for suppressing the analog signal to generate a zero signal in said readout means when a carpet component known to have no latex coating is placed between the source and the detector and means for linearly relating the inverted and suppressed analog signal to the amount of latex on the moving carpet.

22. A method of determining the amount of a substance containing atoms of a non-radioactive element of atomic number of 11 or greater applied to a fabric matrix which comprises:

a. providing a source of radiation which emits a single predominant, monoenergetic radiation within the range of from about 12 to about 19 Kev;

b. providing a charge pulse detector spaced apart from the source and aligned therewith so as to receive radiation therefrom, said detector being sensitive to said radiation and generating a pulse output which varies in amplitude with the energy of said radiation and having a resolution at least as sharp as about 15 percent within the range of from about 12 to about 19 Kev;

c. positioning said fabric matrix and applied substance between said source and detector whereby a portion of said radiation emitted by said source passes through said fabric matrix and substance into said detector;

d. providing readout means connected to said detector; and e. electronically relating said detector output to the amount of substance applied to said fabric matrix and generating a signal in said readout means in response to said relationship.

23. The method of claim 22 wherein said matrix is a carpet, said substance is a latex coating and said non-radioactive element is selected from a group consisting essentially of calcium, aluminum or mixtures thereof.

24. The method of claim 22 wherein step (e) includes converting the pulsed output of the detector to an analog signal.

25. The method of claim 24 wherein step (e) includes inverting the analog signal.

26. The method of claim 22 wherein step (e) includes generating a zero signal in the readout means when a matrix known to be substantially free of the substance is placed between the source and the detector.

27. The method of claim 22 wherein step (e) includes electronically rejecting detector output resulting from detection of radiation having an energy less than a first preselected level and greater than a second preselected level.

28. The method of claim 22 wherein the detector is of the type having a high voltage wire suspended in a chamber containing an atmosphere predomonantly of a noble gas and the balance, carbon dioxide.

29. The method of claim 28 wherein the noble gas is krypton.

30. The method of claim 22 wherein step (e) includes linearly relating the detector output to the amount of substance applied to the matrix.

31. The method of claim 30 wherein step (e) includes prior to said linearly relating step, converting the pulsed output of the detector to an analog signal, inverting the analog signal, and adjusting the analog signal to generate a zero signal when a matrix known to be substantially free of said substance is placed between the source and the detector.

32. The method of claim 31 including electronically rejecting detector output resulting from detection of radiation having an energy less than a first preselected level and greater than a second preselected level, said rejecting step being carried out prior to said converting step.

33. The method of claim 22 wherein the radiation source provided includes a primary source of radiation having an energy greater than about 19 Kev and a target which fluoresces when exposed to the primary source to produce the monoenergetic radiation within the range of from about 12 to about 19 Kev.

34. The method of claim 33 wherein the primary source and the target are mutually selected so that the energy of the predominant radiation of the primary source is from about 2 to about 10 times the energy of the monoenergetic radiation of the target, and wherein the half life of the primary source is at least about 10 years.

35. The method of claim 33 wherein the primary source is americium-241 or a compound thereof.

36. The method of claim 35 wherein the target is zirconium.

37. The method of claim 36 wherein the output of the detector is linearly related to the amount of substance applied to the matrix.

38. The method of claim 37 including the steps, prior to said linearizing steps, of converting the pulsed output of the detector to an analog signal, inverting the analog signal, and adjusting the analog signal to generate a zero signal when a matrix known to be substantially free of said substance is placed between the source and the detector.

39. The method of claim 38 including, prior to said converting step, electronically rejecting detector output resulting from detection of radiation having an energy less than a first preselected level and greater than a second preselected level.

40. The method of claim 36 wherein the detector provided is of the type having a high voltage wire suspended in a chamber containing an atmosphere predominantly of a noble gas and the balance, carbon dioxide.

41. The method of claim 40 wherein the noble gas is krypton.

42. The method of claim 41 wherein the substance is a latex coating, the fabric matrix is a moving segment of carpet and the non-radioactive element is selected from a group consisting essentially of a calcium compound, an aluminum compound or mixture thereof, and step (e) includes electronically rejecting detector output resulting from detection of radiation having an energy less than a first preselected level and greater than a second preselected level, converting the pulsed output which has not been rejected to an analog signal, inverting the analog signal, suppressing the analog signal to generate a zero signal when a reference sample of carpet having no latex is placed between the source and the detector, linearizing said inverted and suppressed analog signal, and generating a signal in visible readout means in response to said linearized signal.

43. The method of claim 41 wherein the substance contains calcium carbonate.

44. The method of claim 41 wherein the substance contains alumina trihydrate.

45. The method of claim 41 wherein the substance contains alumina trihydrate and calcium carbonate.

* * * * *

UNITED STATES PATENT AND TRADEMARK OFFICE
CERTIFICATE OF CORRECTION

PATENT NO. : 4,066,898
DATED : January 3, 1978
INVENTOR(S) : Arthur J. Kamp et al.

It is certified that error appears in the above-identified patent and that said Letters Patent are hereby corrected as shown below:

Column 5, line 40, delete "$i_t$" and insert --$I_t$--.

Column 7, line 46, after the word "radiation" insert the words --versus the higher energy radiation--.

Column 9, Claim 6, line 35, delete "scond" and insert --second--.

Column 11, Claim 28, line 27, delete "predomonantly" and insert --predominantly--.

Signed and Sealed this

Ninth Day of May 1978

[SEAL]

Attest:

RUTH C. MASON
Attesting Officer

LUTRELLE F. PARKER
Acting Commissioner of Patents and Trademarks